US010803722B2

(12) United States Patent
Beszteri et al.

(10) Patent No.: US 10,803,722 B2
(45) Date of Patent: Oct. 13, 2020

(54) EMERGENCY DATA DELIVERY

(71) Applicant: Nokia Technologies Oy, Espoo (FI)

(72) Inventors: Istvan Beszteri, Espoo (FI); Ari Aarnio, Espoo (FI)

(73) Assignee: Nokia Technologies Oy, Espoo (FI)

( * ) Notice: Subject to any disclaimer, the term of this patent is extended or adjusted under 35 U.S.C. 154(b) by 0 days.

(21) Appl. No.: 15/781,697

(22) PCT Filed: Dec. 10, 2015

(86) PCT No.: PCT/FI2015/050870
§ 371 (c)(1),
(2) Date: Jun. 5, 2018

(87) PCT Pub. No.: WO2017/098078
PCT Pub. Date: Jun. 15, 2017

(65) Prior Publication Data
US 2018/0365958 A1 Dec. 20, 2018

(51) Int. Cl.
G08B 21/04 (2006.01)
H04W 4/80 (2018.01)
H04L 29/08 (2006.01)
H04W 76/50 (2018.01)
G08B 6/00 (2006.01)
(Continued)

(52) U.S. Cl.
CPC .......... *G08B 21/0453* (2013.01); *G08B 3/10* (2013.01); *G08B 3/1016* (2013.01); *G08B 6/00* (2013.01);
(Continued)

(58) Field of Classification Search
CPC .... G08B 21/0453; G08B 3/10; G08B 3/1016; G08B 6/00; G16H 10/60; G16H 10/65;
(Continued)

(56) References Cited

U.S. PATENT DOCUMENTS 8,562,489 B2 * 10/2013 Burton ................... G04F 10/00
482/9
8,787,867 B2 * 7/2014 Bleckert ............... H04W 12/06
455/404.1
(Continued)

FOREIGN PATENT DOCUMENTS

WO 2013/134845 A1 9/2013

OTHER PUBLICATIONS

Lv et al., "iCare: A Mobile Health Monitoring System for the Elderly", IEEE/ACM Int'l Conference on & Int'l Conference on Cyber, Physical and Social Computing (CPSCom) Green Computing and Communications (GreenCom), Dec. 18-20, 2010, 7 pages.
(Continued)

*Primary Examiner* — Nader Bolourchi
(74) *Attorney, Agent, or Firm* — Mintz Levin Cohn Ferris Glovsky and Popeo, P.C.

(57) ABSTRACT

According to an example embodiment, a method is provided, the method comprising receiving, in a user device, over a first wireless link from a wearable device, a beaconing message that includes emergency information concerning a user wearing the wearable device, initiating, in the user device, in response to said beaconing message, an emergency call to a destination that hosts an emergency service entity, and relaying, by the user device, the emergency information received in the beaconing message from the wearable device to the emergency service entity via a second wireless link.

20 Claims, 10 Drawing Sheets

(51) Int. Cl.
  *G08B 3/10* (2006.01)
  *H04W 4/90* (2018.01)
  *G16H 10/65* (2018.01)
  *H04W 4/38* (2018.01)
  *G16H 80/00* (2018.01)
  *G16H 10/60* (2018.01)
  *H04W 76/14* (2018.01)
  *H04W 84/18* (2009.01)

(52) U.S. Cl.
  CPC ............. *G16H 10/65* (2018.01); *G16H 80/00* (2018.01); *H04L 29/08* (2013.01); *H04W 4/38* (2018.02); *H04W 4/80* (2018.02); *H04W 4/90* (2018.02); *H04W 76/50* (2018.02); *G16H 10/60* (2018.01); *H04W 76/14* (2018.02); *H04W 84/18* (2013.01)

(58) Field of Classification Search
  CPC ......... G16H 80/00; H04L 29/08; H04W 4/38; H04W 4/80; H04W 4/90; H04W 76/14; H04W 76/50; H04W 84/18
  See application file for complete search history.

(56) References Cited

U.S. PATENT DOCUMENTS

| | | | |
|---|---|---|---|
| 9,106,672 B2 * | 8/2015 | Zhang | .................... H04W 4/02 |
| 9,330,554 B2 * | 5/2016 | Calvar Anton | ........... B63C 9/08 |
| 9,888,842 B2 * | 2/2018 | White | .................... A61B 3/113 |
| 9,911,308 B2 * | 3/2018 | Edwards | ................ A61M 5/20 |
| 2012/0220835 A1 | 8/2012 | Chung | |
| 2014/0106699 A1 | 4/2014 | Chitre et al. | |
| 2014/0143064 A1 | 5/2014 | Tran | |
| 2014/0295786 A1 | 10/2014 | Maier et al. | |
| 2014/0327540 A1 | 11/2014 | Shin et al. | |
| 2014/0368601 A1 | 12/2014 | deCharms | |
| 2015/0039040 A1 | 2/2015 | Cowan et al. | |
| 2015/0140954 A1 * | 5/2015 | Maier | ................... H04W 4/025 455/404.2 |
| 2015/0350848 A1 | 12/2015 | Eramian | |
| 2019/0347923 A1 * | 11/2019 | Mckinley | ............... G08B 25/10 |

OTHER PUBLICATIONS

Wu et al., "WAITER: A Wearable Personal Healthcare and Emergency Aid System", Sixth Annual IEEE International Conference on Pervasive Computing and Communications, Mar. 17-21, 2008, pp. 680-685.

"Bluetooth Specification Version 4.1", Specification of the Bluetooth system, Dec. 3, 2013, 2684 pages.

International Search Report and Written Opinion received for corresponding Patent Cooperation Treaty Application No. PCT/FI2015/050870, dated Mar. 30, 2016, 16 pages.

* cited by examiner

400

Receive, in a destination hosting an emergency service entity, an emergency call from a user device

410

Receive, in the emergency service entity from the user device, emergency information concerning a user of a wearable device, which emergency information includes information that originates from the wearable device

420

Receive, in the emergency service entity from the user device, further emergency information concerning said user

EMERGENCY DATA DELIVERY

CROSS REFERENCE TO RELATED APPLICATION

This application is a U.S. National Stage National Stage Application, filed under 35 U.S.C. § 371, of International Patent Application No. PCT/FI2015/050870, filed on Dec. 10, 2015 and entitled "Emergency Data Delivery." The disclosure of International Patent Application No. PCT/FI2015/050870 is incorporated herein by reference in its entirety.

BACKGROUND

In case of a medical emergency, immediate medical attention that matches the needs of a patient is in many cases a matter of life and death. Therefore, a technique that enables timely provision of information concerning conditions that may affect the type and urgency of the medical attention the patient needs may be a life-saving one.

SUMMARY

According to an example embodiment, a method is provided, the method comprising receiving, in a user device, over a first wireless link from a wearable device, a beaconing message that includes emergency information concerning a user wearing the wearable device, initiating, in the user device, in response to said beaconing message, an emergency call to a destination that hosts an emergency service entity, and relaying, by the user device, the emergency information received in the beaconing message from the wearable device to the emergency service entity via a second wireless link.

According to another example embodiment, an apparatus is provided, the apparatus comprising a first communication apparatus for wireless communication via a first wireless link and a second communication apparatus for wireless communication via a second wireless link, the apparatus configured to receive, over the first wireless link from a wearable device, a beaconing message that includes emergency information concerning a user wearing the wearable device, initiate, in response to said beaconing message, an emergency call to a destination that hosts an emergency service entity, and relay the emergency information received in the beaconing message from the wearable device to the emergency service entity via the second wireless link.

According to another example embodiment, an apparatus is provided, the apparatus comprising at least one processor and a memory storing a program of instructions, a first communication apparatus for wireless communication via a first wireless link and a second communication apparatus for wireless communication via a second wireless link, wherein the memory storing the program of instructions is configured to, with the at least one processor, cause the apparatus to at least: receive, over the first wireless link from a wearable device, a beaconing message that includes emergency information concerning a user wearing the wearable device, initiate, in response to said beaconing message, an emergency call to a destination that hosts an emergency service entity, and relay the emergency information received in the beaconing message from the wearable device to the emergency service entity via the second wireless link.

According to another example embodiment, an apparatus is provided, the apparatus comprising a first wireless communication means for wireless communication via a first wireless link, a second wireless communication means for wireless communication via a second wireless link, and a control means configured to cause the apparatus to receive, over the first wireless link from a wearable device, a beaconing message that includes emergency information concerning a user wearing the wearable device, initiate, in response to said beaconing message, an emergency call to a destination that hosts an emergency service entity, and relay the emergency information received in the beaconing message from the wearable device to the emergency service entity via the second wireless link.

According to another example embodiment, a computer program is provided, the computer program comprising computer readable program code configured to cause performing, when said program code is run on a computing apparatus, a method in a user device, the method comprising receiving, over a first wireless link from a wearable device, a beaconing message that includes emergency information concerning a user wearing the wearable device, initiating, in response to said beaconing message, an emergency call to a destination that hosts an emergency service entity, and relaying the emergency information received in the beaconing message from the wearable device to the emergency service entity via a second wireless link.

The computer program referred to above may be embodied on a volatile or a non-volatile computer-readable record medium, for example as a computer program product comprising at least one computer readable non-transitory medium having program code stored thereon, the program which when executed by an apparatus cause the apparatus at least to perform the operations described hereinbefore for the computer program according to an example embodiment of the invention.

The exemplifying embodiments of the invention presented in this patent application are not to be interpreted to pose limitations to the applicability of the appended claims. The verb "to comprise" and its derivatives are used in this patent application as an open limitation that does not exclude the existence of also unrecited features. The features described hereinafter are mutually freely combinable unless explicitly stated otherwise.

Some features of the invention are set forth in the appended claims. Aspects of the invention, however, both as to its construction and its method of operation, together with additional objects and advantages thereof, will be best understood from the following description of some example embodiments when read in connection with the accompanying drawings.

BRIEF DESCRIPTION OF FIGURES

The embodiments of the invention are illustrated by way of example, and not by way of limitation, in the figures of the accompanying drawings, where

FIG. 5C illustrates a flow diagram according to an example embodiment;

DESCRIPTION OF SOME EMBODIMENTS

Figure 1:
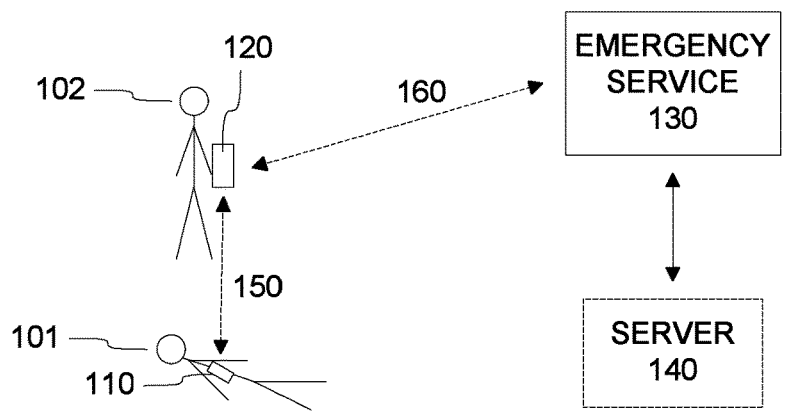
FIG. 1 illustrates a block diagram of some components of an arrangement according to an example embodiment.

FIG. 1 illustrates a block diagram of some components of an exemplifying arrangement 100 that enables delivery of emergency information associated with a person to an emergency service center or to another entity that provides medical services. The delivery of the emergency information in the framework of the arrangement 100 may be referred to as emergency assistance service. The arrangement 100 depicts a wearable device 110 worn by a first user 101, a user device 120 of a second user 102 and an emergency service entity 130. In case of a medical emergency pertaining to the first user 101, for example, a first wireless link 150 between the wearable device 110 and the user device 120 and at least a data transfer regarding emergency information relating to the first user 101 over a second wireless link 160 between the user device 120 and the emergency service entity 130 may be arranged. The user device 120 may further employ the first wireless link 150 and the second wireless link 160 to provide a secure communication channel between the wearable device 110 and the emergency service entity 130 for delivery of emergency information pertaining to the user 101. The arrangement 100 may, optionally, comprise a server device 140 that may store further information pertaining to the first user 101, which further information may be accessible at least in part on basis of the emergency information received vie the secure connection from the wearable device 110.

Although the example arrangement 100 in FIG. 1 depicts the first user 101 and the second user 102 as two different persons, in other examples there may be only a single person involved: i.e. the user 102 of the user device 120 may also wear the wearable device 110 or the user 101 wearing the wearable device 101 may also be the user of the user device 120. In a further example, the arrangement that enables delivery of emergency information may involve a plurality of wearable devices 110 and/or a plurality of user devices 120. In a yet further example, one person (e.g. the user 101 or the user 102) may wear multiple wearable devices 110. In yet another example, the functions of the wearable device 110 are at least in part integrated to the user device 120. Nevertheless, in the following, various non-limiting examples concerning delivery of the emergency information between the wearable device 110 and the emergency service entity 130 are described with references to the arrangement 100, while this choice is made in the interest of editorial clarity and the examples readily generalize into e.g. variations of the arrangement 100 outlined in the foregoing.

Figure 2:
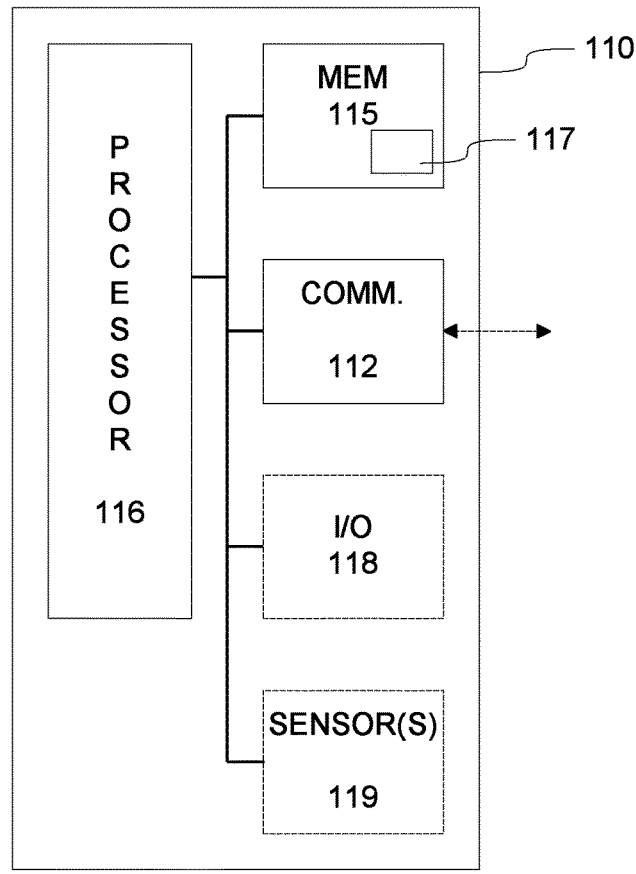
FIG. 2 illustrates a block diagram of some components of an apparatus according to an example embodiment.

FIG. 2 illustrates a block diagram of some components of the wearable device 110 according to an example. The wearable device 110 may comprise further components or portions in addition to those depicted in FIG. 2, whereas the ones depicted therein are ones that are considered in description of some embodiments of the present invention. In an example, the wearable device 110 is arranged in a garment and hence the user 101 may wear the wearable device 110 by wearing the garment. Examples of such garments include any piece of clothing, such a shirt, pants, a hat, gloves that include one or more sensors In such a scenario the garment including the wearable device 110 may be referred to as a smart garment or a piece of smartwear. In another example, the wearable device 110 is provided as a purpose-specific device with a suitable fitting arrangement that enables the user 101 to directly wear it. In a further example, the wearable device 110 is provided in an accessory device that is wearable by the user 101. Non-limiting examples of such accessory devices include headphones, a wrist watch (a smartwatch), a wrist band, an activity tracker, a heart rate monitor device, etc.

The wearable device 110 comprises a processor 116 and a memory 115 for storing data and computer program code 117. The wearable device 110 may further comprise user I/O (input/output) components 118 that may be arranged, possibly together with the processor 116 and a portion of the computer program code 117, to provide a user interface for receiving input from a user of the wearable device 110 and/or providing output to the user of the wearable device 110. The user I/O components 118 may comprise hardware components such as a display, a touchscreen and/or an arrangement of one or more keys or buttons, etc. The user I/O components 118 may be also referred to as peripherals.

The wearable device 110 comprises a communication apparatus 112 for wireless communication with other devices over a wireless link. The communication apparatus 112 may be also referred to as (wireless) communication means 112. The communication apparatus 112 may enable, for example, wireless communication with other devices by using a wireless communication technique or protocol that enables a point-to-point or a point-to-multipoint wireless connection with another device. The wearable device 110 is hence capable of communicating with other devices that are equipped with a wireless communication apparatus using the same technique/protocol, e.g. with the user device 120, as will be described in more detail later in this text. The wearable device 110 may comprise one or more further communication apparatuses for wireless or wired communication with other devices. The communication apparatus 112, possibly together with one or more further communication apparatuses, may be considered to (at least conceptually) constitute a communication portion within the wearable device 110.

The processor 116 may be arranged to provide a control function for controlling operation of the wearable device 110 at least in accordance with a portion of the computer program code 117 and possibly further e.g. in accordance with the user input received via the user I/O components 118 and/or in accordance with information received via the communication portion. This control function may be also referred to as control means (of the wearable device 110). In an example, at least part of the control function is provided by a software application that, when executed by the processor 116, causes the wearable device 110 to facilitate transfer of the emergency information from the wearable device 110 via the user device 120 to the emergency service entity 130. This aspect of the operation of the control means may be referred to as emergency assistant data source function or emergency assistant data source application, operation of which will be described in further detail by examples provided later in this text.

The wearable device 110 may further comprise one or more sensors 119. The sensor(s) 119 may include one or more sensors for measuring respective one or more vital signs of the first user 101, such as one or more of body temperature, heart rate, blood pressure, photoplethysmogram (ppg). Such information may serve to provide valuable information about medical condition of the user 101 in case of a medical emergency. As another example, alternatively or additionally, the sensor(s) 119 may comprise one or more sensors for measuring respective one or more environmental characteristics, such as ambient temperature, air pressure, $CO_2$ level, etc. Such information may serve to provide valuable information about environmental conditions around the user 101 in case of a medical emergency. Alternatively, instead of the wearable device 110 directly hosting the one or more sensors 119, the wearable device 110 may be communicatively coupled to one or more other wearable components, each of which comprises one or more of the one or more sensors 119 described in the foregoing. Each of the one or more sensors 119 may be arranged to provide a respective time series of measurement values that are descriptive of the value of the respective vital sign or environmental characteristic over time. The time series of measurement values so obtained may be stored e.g. in the memory 115 for subsequent use as emergency information.

In one example, one or more sensor measurements can be analyzed by the processor 116 in the wearable device 110. Based on the analysis a message generated in the wearable device 110 may indicate reason for the emergency or indicate a need for a piece of equipment or a substance that may be necessary to help the first user 101 wearing the wearable device 110 in an emergency. In another example, an indication of the needed or necessary piece of equipment or substance may be included in the message sent from the wearable device 110 based on a potential need that may be e.g. based on the measurement values from the sensors 119 or on predefined knowledge such as doctor's orders. As an example, if the first user 101 suffers from diabetes, then e.g. an indication of insulin as potential medicament may be included in the message. In addition, an indication of insulin may also serve as an indication of an aspect related to the first user 101 to be checked at a high priority. Consequently the wearable device 110 may provide in a digital message a suggestion regarding a way to help the first user 101 in case of an emergency.

Figure 3:
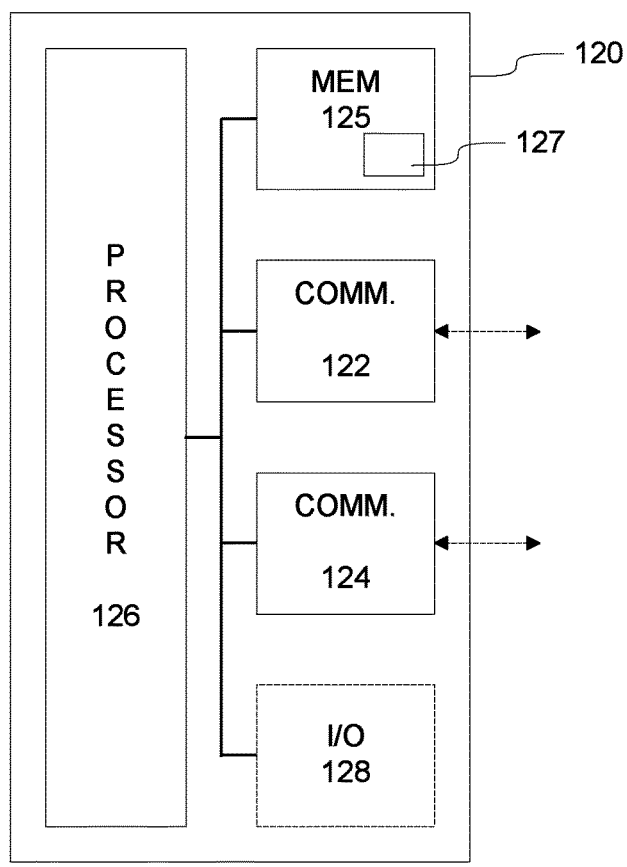
FIG. 3 illustrates a block diagram of some components of an apparatus according to an example embodiment.

FIG. 3 illustrates a block diagram of some components of the user device 120 according to an example. The user device 120 may comprise further components or portions in addition to those depicted in FIG. 3, whereas the ones depicted therein are ones that are considered in description of some embodiments of the present invention. In an example, the user device 120 is a portable mobile device that is typically frequently carried with the user 102 or worn by the user 102, such as a mobile phone, a smartphone, a portable gaming device, a portable music or media player, a portable navigation device, a smartwatch, a personal digital assistant (PDA), a tablet computer, a laptop computer, etc.

The user device 120 comprises a processor 126 and a memory 125 for storing data and computer program code 127. The user device 120 may further comprise user I/O components 128 that may be arranged, possibly together with the processor 126 and a portion of the computer program code 127, to provide a user interface for receiving input from a user of the user device 120 and/or providing output to the user of the user device 120. The user I/O components 128 may comprise hardware components such as a display, a touchscreen, a touchpad, a mouse, a keyboard, and/or an arrangement of one or more keys or buttons, etc. The user I/O components 128 may be also referred to as peripherals.

The user device 120 comprises a first communication apparatus 122 and a second communication apparatus 124, each enabling wireless communication with other devices over a respective wireless link. The communication apparatus 122, 124 may be also referred to as respective (wireless) communication means 122, 124. The first communication apparatus 122 may enable, for example, wireless communication with other devices by using a wireless communication technique or protocol that enables a point-to-point or a point-to-multipoint wireless connection with another device (e.g. an ad-hoc connection), whereas the second communication apparatus 124 may enable, for example, wireless access to a computer network that, in turn, enables connection with other devices connected to the computer network. In particular, the first communication apparatus 122 may enable connection with the wearable device 110 via the first wireless link 150 and the second communication apparatus 124 may enable the second wireless link 160 with the emergency service entity 130. The user device 120 may comprise one or more further communication apparatuses for wireless or wired communication with other devices. The first and second communication apparatuses 122, 124, possibly together with one or more further communication apparatuses, may be considered to (at least conceptually) constitute a communication portion within the user device 120.

The processor 126 may be arranged to provide a control function for controlling operation of the user device 120 at least in accordance with a portion of the computer program code 127 and possibly further e.g. in accordance with the user input received via the user I/O components 128 and/or in accordance with information received via the communication portion. This control function may be also referred to as control means (of the user device 120). In an example, at least part of the control function is provided by a software application that, when executed by the processor 126, causes the user device 120 to facilitate transfer of the emergency information between the wearable device 110 and the emergency service entity 130. This aspect of the operation of the control means may be referred to as emergency assistant gateway function or emergency assistant gateway application, operation of which will be described in further detail by examples provided later in this text.

Figure 4:
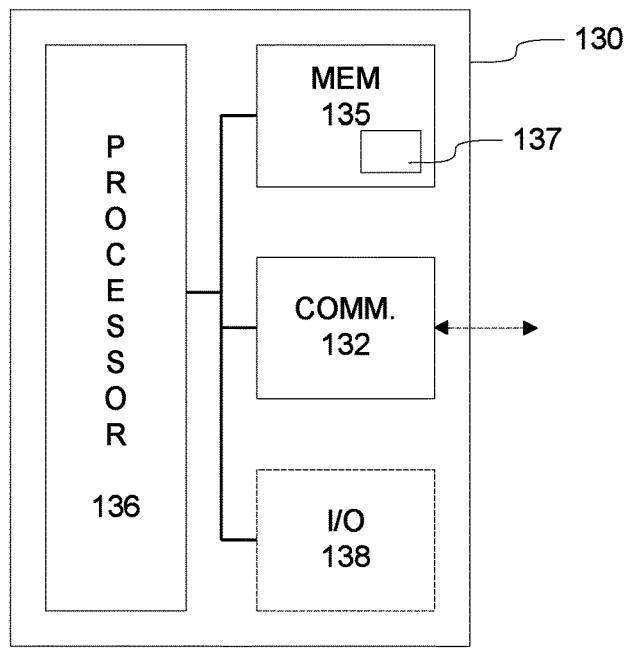
FIG. 4 illustrates a block diagram of some components of an apparatus according to an example embodiment.

FIG. 4 illustrates a block diagram of some components of the emergency service entity 130 according to an example. The emergency service entity 130 may comprise further components or portions in addition to those depicted in FIG. 4, whereas the ones depicted therein are ones that are considered in description of some embodiments of the present invention. In an example, the emergency service entity 130 is provided as a computing device arranged for use of emergency service personnel e.g. in an emergency service center, in a hospital, in an emergency vehicle (such as an ambulance, in a police car, a fire engine) etc. Depending on the usage environment, the emergency service entity 130 may be embodied in one of a number of ways. As an example, the emergency service entity 130 may be provided in a portable user device that is typically frequently carried with the emergency personnel, which may be e.g. a specific-purpose device designed to operate as the emergency service entity 130 or a general purpose device arranged to operate as the emergency service entity 130. For the latter case, the device may be e.g. a mobile phone, a smartphone, a portable navigation device, a personal digital assistant (PDA), a tablet computer, etc. As another example, the emergency service entity 130 may be provided in a semi-stationary device, i.e. a device that is basically a portable device but that is not typically moved from its location, that is only infrequently relocated from one place to another and/or that is used within a restricted geographical area (such as within premises of an emergency service center or a hospital), such as a desktop computer, a laptop computer, a tablet computer, etc. In a further example, the emergency service entity 130 is provided in or as a device that is installed in an emergency vehicle.

The emergency service entity 130 comprises a processor 136 and a memory 135 for storing data and computer program code 137. The user device 130 may further comprise user I/O components 138 that may be arranged, possibly together with the processor 136 and a portion of the computer program code 137, to provide a user interface for receiving input from a user of the emergency service entity 130 and/or providing output to the user of the emergency service entity 130. The user I/O components 138 may comprise hardware components such as a display, a touchscreen, a touchpad, a mouse, a keyboard, and/or an arrangement of one or more keys or buttons, etc. The user I/O components 138 may be also referred to as peripherals.

The emergency service entity 130 comprises a communication apparatus 132 for wireless or wired communication with other devices via a computer network. The communication apparatus 132 may be also referred to as respective communication means 132. In particular, the communication apparatus 132 may enable connection with the user device 120 (via the second communication apparatus 124) The emergency service entity 130 may comprise one or more further communication apparatuses for wireless or wired communication with other devices. The communication apparatus 132, possibly together with one or more further communication apparatuses, may be considered to (at least conceptually) constitute a communication portion within the emergency service entity 130.

The processor 136 may be arranged to provide a control function for controlling operation of the emergency service entity 130 at least in accordance with a portion of the computer program code 137 and possibly further e.g. in accordance with the user input received via the user I/O components 138 and/or in accordance with information received via the communication portion. This control function may be also referred to as control means (of the emergency service entity 130). In an example, at least part of the control function is provided by a software application that, when executed by the processor 136, causes the emergency service entity 130 to facilitate transfer of the emergency information to and/or from the wearable device 110 via the user device 120. This aspect of the operation of the control means may be referred to as emergency assistant data destination function or emergency assistant data destination application, operation of which will be described in further detail by examples provided later in this text.

The first wireless link 150 between the wearable device 110 and the user device 120 (e.g. the wireless link between the communication apparatuses 112 and 122) may be provided by employing a suitable short-range wireless communication technique or protocol. Such a wireless link may also be referred to as a local wireless link. The term short-range wireless communication as used herein refers to a wireless communication technique or protocol that enables typical operating range in the scale of tens of meters, e.g. up to 100 meters. However, especially in an indoor environment, the operating range of such short-range wireless communication technique/protocol may be significantly shorter e.g. due to walls and other stationary structures as well as furniture etc. that are likely to partially block or interfere with the radio communication between the two devices. On the other hand, in favorable conditions in outdoor use the operating range may extend to several hundreds of meters.

Examples of such a wireless technique/protocol include the Bluetooth Basic Rate/Enhanced Data Rate (BT BR/EDR) protocol and the Bluetooth Low Energy (BLE) protocol, both specified e.g. in the Bluetooth Specification Version 4.1, Covered Core Package version: 4.1 (publication date 3 Dec. 2013), incorporated herein by reference in its entirety. In the following, this document is referred to as a Bluetooth Specification. The BLE is also commonly referred to as Bluetooth LE or as Bluetooth Smart. A further example of such a wireless technique/protocol is Wireless Local Area Network (WLAN) technology specified e.g. in IEEE 802.11 specifications (where the acronym IEEE stands for the Institute of Electrical and Electronics Engineers). Further examples of applicable wireless techniques/protocols include Z-wave, ZigBee, ANT (a proprietary multicast sensor network technology), near field communication (NFC) and radio-frequency identification (RFID). However, the BT BR/EDR, BLE, WLAN, NFC and RFID technologies serve as illustrative and non-limiting examples in this regard, and the description generalizes into any short-range wireless communication technique/protocol.

The communication apparatus 124 may be arranged to employ any suitable wireless access technology known in the art to establish a connection to a computer network that further connects the user device 120 to the emergency service entity 130. As an example in this regard, the communication apparatus 124 may be arranged to employ the WLAN technology referred to in the foregoing to establish the second wireless link 160 with a wireless access point in its vicinity, which second wireless link 160 enables the user device 120 to access a computer network that further enables connection to the emergency service entity 130. As another example, the communication apparatus 124 may be arranged to employ a cellular access technology known in the art to establish a wireless link with a base station of a cellular network, which wireless link enables the user device 120 to access a computer network that further enables connection to the emergency service entity 130.

The wearable device 110 may store the emergency information in the memory 115. The emergency information may serve as data to be delivered via the user device 120 to the emergency service entity 130 in context of the emergency assistance service within the framework of the arrangement 100. The emergency information includes personal information associated with the first user 101 and medical information associated with the first user 101. The emergency information may further include environmental information that is descriptive of one or more environmental characteristics in vicinity of the wearable device 110.

The personal information comprises at least one user identifier that uniquely identifies the first user 101 at least within the framework of the emergency assistance service. As an example, a user identifier may comprise an identifier assigned for the first user 101 in context of the emergency assistance service. As another example, additionally or alternatively, a user identifier may comprise an identifier assigned for the first user 101 in some other context, e.g. a personal identification or a medical identifier assigned for the first user 101 by a national or regional authority or a social security number assigned for the first user 101 by a national or regional authority. The personal information may further include personal details associated with the first user 101, such as one or more of the following: name, gender, date of birth, age, nationality, in case of emergency (ICE) contact information, etc.

The user 101 may have pre-registered himself/herself with the emergency service entity 130 in the context of the emergency assistance service described herein by submitting his/her user identifier thereto, thereby enabling the emergency service entity 130 to subsequently recognize the first user 101 on basis of the user identifier received in the emergency information. Additionally, the first user 101 may pre-register also a device identifier assigned for the wearable device (e.g. a MAC address of the communication apparatus 112 or another suitable identifier associated with the wearable device 110 that is known to the emergency service entity 130) with the emergency service entity 130, thereby enabling the emergency service entity 130 to subsequently recognize the first user 101 on basis of the device identifier received in or together with the emergency information.

The medical information may include one or more of the following: static medical information associated with the first user 101, dynamically updated medical information associated with the first user 101 and at least part of the medical history information associated with the first user 101. Examples of each these types of medical information are provided in the following:

The static medical information includes one or more pieces of medical information associated with the first user 101 that do not vary over time or that are only infrequently updated. The static medical information may include e.g. one or more of the following: weight of the first user 101, height of the first user 101, blood type of the first user 101, etc. The updating of static medical information by the user may involve e.g. entering new or updated values via the user interface of the wearable device 110 or uploading new or updated values from another device via a wireless link by using an aspect of the emergency assistant data source function/application.

The dynamically updated medical information includes one or more pieces of information that are indicative of the current medical status of the first user 101. In this regard, the dynamically updated medical information may include respective indications of current values of one or more vital signs of the first user 101. Examples of such vital signs include body temperature, heart rate and blood pressure. The current value for a given vital sign may include the most recently obtained or measure value for the given vital sign. Indication of the current value of the given vital sign may be obtained, for example, from a respective one of the sensor(s) 119 that may be provided in the wearable device 110 or that may be communicatively coupled to the wearable device 110.

The medical history information may include one or more pieces of information that indicate of general medical status of the first user 101 and/or one or more pieces of information that indicate history of values of one or more vital signs of the first user 101. An example of the former is an indication of a chronic medical condition or illness, while examples of the latter include respective indications of past values of one or more vital signs of the first user 101. The indications of the past values for a given vital sign may include, for example, as one or more of the following: a time series of past values that cover a predefined time period (e.g. predefined time period immediately preceding the present time), an average of the past values over the predefined time period, a maximum of the past values over the predefined time period, a minimum of the past values over the predefined time period, etc. The indications of the past values of the given vital sign may be obtained, for example, from a respective one of the sensor(s) 119 that may be provided in the wearable device 110 or that may be communicatively coupled to the wearable device 110.

The environmental information may include respective current and/or past values for one or more environmental characteristics in vicinity of the wearable device 110. Examples of such environmental characteristics include ambient temperature, air pressure, CO level and $CO_2$ level. The current value for a given environmental characteristic may include the most recently obtained or measure value for the given environmental characteristic. The indications of the current and/or past values of the given environmental characteristics may be obtained, for example, from a respective one of the sensor(s) 119 that may be provided in the wearable device 110 or that may be communicatively coupled to the wearable device 110.

The emergency information may be stored in the wearable device 110 (e.g. in the memory 115) in an emergency information database that includes a plurality of database entries, each of which includes a respective piece (or respective pieces) of emergency information together with one or more data type identifiers that serve to identify the type of emergency information stored in that database entry. The one or more data type identifiers for a database entry may include an emergency information class identifier that assigns the database entry to be one of predefined emergency information classes (e.g. to one of personal information, static medical information, medical history information, dynamically updated medical information, environmental information) and possibly further an emergency information sub-class identifier that assigns the database entry to one of predefined medical information sub-classes in dependence of the assigned emergency information class (e.g. a database entry assigned as static medical information may be further assigned into one of weight, height, blood type, etc.).

The emergency information database may be provided as part of a generic database that also comprises other information in addition to the emergency information. In such a scenario, the database entries that represent the emergency information may be provided with a further data type identifier that identifies the respective database entry to represent emergency information.

Regardless of the way of storing the emergency information in the wearable device 110, e.g. in the dedicated emergency information database or as part of a generic database that also includes the database entries that constitute the emergency information, there may be a mechanism for controlling availability of the emergency information to the emergency service entity 130. In particular, such mechanism may enable indicating those pieces of emergency information that are to be provided to the emergency service entity 130 in case of a medical emergency. As an example, such mechanism may involve including in database entries that represent emergency information an availability indicator that indicates the availability (or lack thereof) of the respective piece(s) of emergency information, whereas in case of providing the emergency information database as part of a generic database such mechanism may, alternatively, involve using the data type identifier to identify only the pieces of medical information that are available for the emergency service entity 130 to represent emergency information. The availability indications may be set, for example, in accordance with user input received via the user interface of the wearable device 110, which may be enabled e.g. by an aspect of the emergency assistant data source application.

Figure 5A:
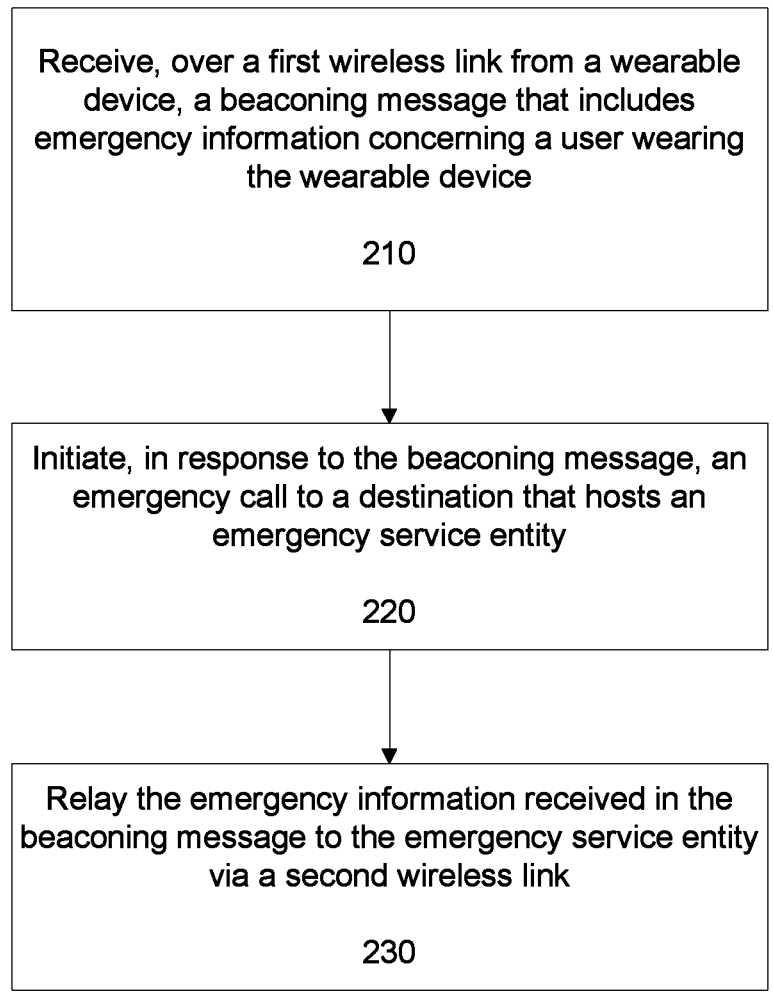
FIG. 5A illustrates a flow diagram according to an example embodiment.

FIG. 5A illustrates a flow diagram according to an example embodiment, depicted as steps of a method 200. The method 200 comprises receiving, in the user device 120 over the first wireless link 150, a beaconing message that includes emergency information concerning the user 101 of the wearable device 110, as indicated in block 210. The method 200 further comprises initiating, in the user device 120, in response to the beaconing message, an emergency call to a destination that hosts the emergency service entity 130, as indicated in block 220. The method 200 further comprises relaying, by the user device 120, the emergency information received in the beaconing message from the wearable device 110 to the emergency service entity 130 via the second wireless link 160, as indicated in block 230.

Figure 5B:
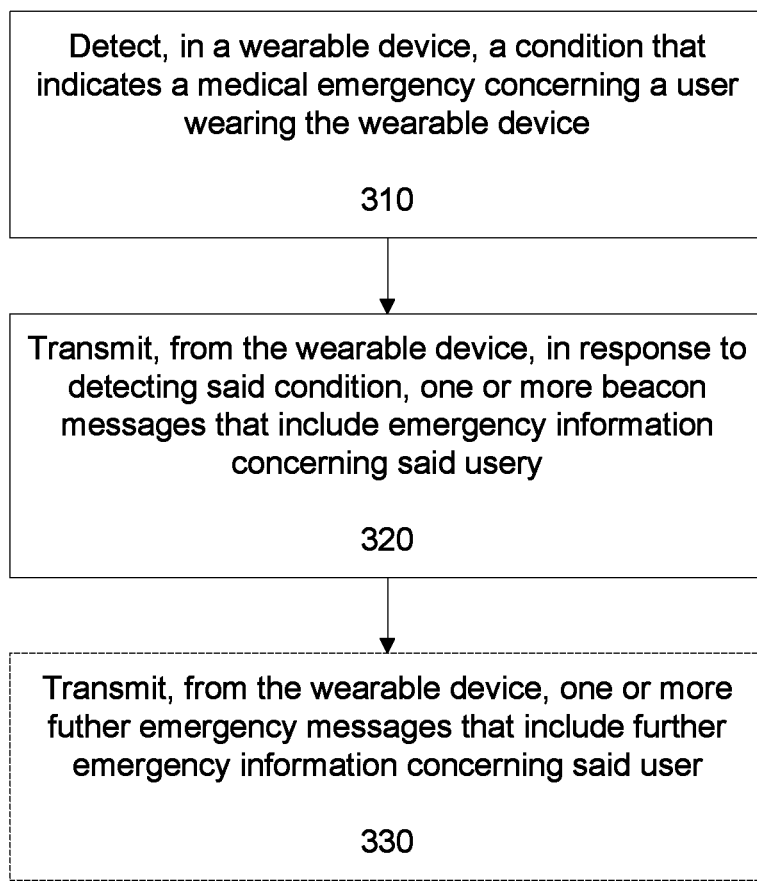
FIG. 5B illustrates a flow diagram according to an example embodiment.

FIG. 5B illustrates a flow diagram according to another example embodiment, depicted as steps of a method 300. The method 300 comprises detecting, in the wearable device 110, a condition that indicates a medical emergency concerning the user 101 wearing the wearable device 110, as indicated in block 310. The method 300 further comprises transmitting from the wearable device 110, in response to detecting the medical emergency-indicating condition, one or more beaconing messages that include the emergency information concerning the user 101 of the wearable device 110, as indicated in block 320. As an example in this regard, detection of a condition that indicates medical emergency of the user 101 may comprise receiving indications of one or more of the sensors 119. The method 300 may further comprise transmitting, from the wearable device 110 to the user device 120, further emergency messages that carry (further) emergency information concerning the user 101 of the wearable device 110, as indicated in block 330.

FIG. 5C illustrates a flow diagram according to another example embodiment, depicted as steps of a method 400. The method 400 comprises receiving, in a destination hosting the emergency service entity 130, an emergency call from the user device 120, as indicated in block 410. The method 400 further comprises receiving, in the emergency service entity 130 from the user device 120, the emergency information concerning the user 101 of the wearable device 110, which emergency information includes information that originates from the wearable device 110, as indicated in block 420. The emergency information is transferred from the user device 120 to the emergency service entity 130 via a communication channel that separate and independent of a voice channel provided by the emergency call. The method 400 may further comprise receiving, from the user device 120, further emergency information concerning the user 101 of the wearable device 110, as indicated in block 430. The further emergency information may be received, for example, in response to one or more explicit requests transmitted from the emergency service entity 130.

The operations described with references to blocks 210, 220 and 230 of the method 200, blocks 310, 320 and 330 of the method 300 and/or blocks 410, 420 and 430 of the method 400 in the foregoing may be embodied and varied in a number of ways, as will be described in the non-limiting examples in the following.

In an example, the emergency information may be included in its entirety in a single message beaconing message transmitted from the wearable device 110 over the first wireless link 150. This single message that includes the emergency information may be, alternatively, referred to as a first emergency message. In another example, the emergency information may be transmitted from the wearable device 110 to the user device 120 in a plurality of messages. In this example, the emergency messages that follow the beaconing message (i.e. the first emergency message) may be referred to as further emergency messages. Each of the beaconing message and the further emergency messages may carry a respective predefined emergency identifier (emergency ID) that identifies the message as the beaconing message or as the further emergency message. An emergency ID may comprise a respective predefined character string, numerical value, bit pattern, etc. The emergency ID may be included in a predefined position or location within the beaconing message or the further emergency message or within a packet or other data structure used to carry the beaconing message or the further emergency message.

The amount of emergency information included in the beaconing message or in the further emergency may depend on characteristics of the wireless communication technology employed to provide the first wireless link. As a non-limiting example, usage of the BLE technology and advertising messages thereof as the beaconing messages and/or the further emergency messages allows inclusion of max. 31 bytes of emergency information per message. As another example, in addition to possible transmission bandwidth limitations also the power consumption of the communication apparatus 112 of the wearable device 110 may pose limitations to the amount and/or frequency of beaconing messages and/or further emergency messages transmitted from the wearable device 110.

The transfer of emergency messages and further emergency messages over the first wireless link 150 may be carried out e.g. by using a predefined first communication protocol dedicated for this purpose or by using a generic communication protocol such that it is arranged or tailored to serve this purpose of delivering the emergency information in context of the emergency assistance service described herein. In a scenario where transmission of further emergency messages is available, he transfer of the emergency information from the wearable device 110 to the emergency service entity 130 may be carried by out using a predefined second communication protocol designed for this purpose or by using a generic communication protocol or communication framework such that it is arranged or tailored to serve this purpose. The emergency assistant data destination application (in the emergency service entity 130), the emergency assistant gateway application (in the user device 120) and the emergency assistant data source application (in the wearable device 120) may be arranged to implement respective aspect of the second communication protocol or framework to enable transfer of the emergency information from the wearable device 110 to the emergency service entity 130 via the user device 120. In an example, each of the emergency assistant gateway application, the emergency assistant data source application and the emergency assistant data destination application may be e.g. downloaded directly or indirectly to the respective device 120, 110, 130 from a suitable online resource for digital distribution of computer software, e.g. from an app store. In another example, the emergency assistant data source application may be downloaded by the user device 120 e.g. from the app store and forwarded to wearable device 110 over a wireless connection enabled by the communication apparatuses 112 and 122.

The second communication protocol may enable the emergency service entity 130 to request one or more desired pieces of the emergency information from the wearable device 110, whereas the wearable device 110 may respond the request by providing the requested pieces of emergency information—as far as they are available in the wearable device 110—to the emergency service entity 130 in one or more further emergency messages. As a few examples, a request from the emergency service entity 130 may involve one of the following:

- a request for all emergency information available in the wearable device 110;
- a request for all personal information available in the wearable device 110;
- a request for a specified piece of the personal information or the medical information;
- a request for all medical information available in the wearable device 110;
- a request for a specific piece of medical information available in the wearable device 110;
- a request for all environmental information available in the wearable device 110;
- a request for a specified piece of environmental information
- a request for enabling a continuous flow of further emergency messages that provide real-time measurement values from the sensors 119 as such or filtered using respective predefined filter procedures until further notice, e.g. until medical help for the first user 101 is available.

As an example, a request may serve as a request for one time delivery of the requested piece(s) of emergency information from the wearable device 110. As another example, e.g. in case of dynamically updated medical information and the environmental information, a request may serve as a request to start provision of periodic updates concerning the requested piece(s) of emergency information. In such a scenario, the request may further specify a time interval at which the periodic updates are to be delivered from the wearable device 110. In case the possibility of periodic updates of emergency information is available, the emergency service entity 130 is further enabled to request a termination of all currently requested periodic updates and/or to request a termination of requested periodic updates for a specified piece of emergency information.

Figure 6:
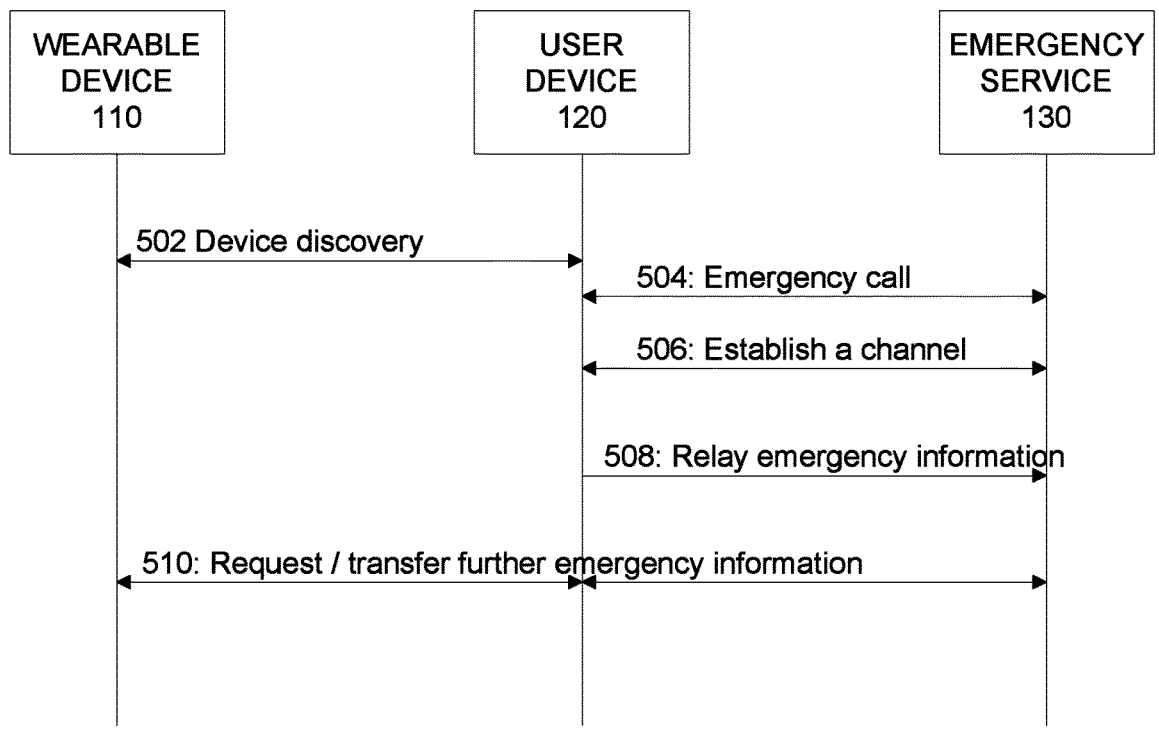
FIG. 6 illustrates a signal sequence diagram according to an example embodiment.

FIG. 6 depicts an example of a signal sequence diagram to enable transfer of the emergency information between elements of the arrangement 100 in context of the emergency assistance service. In step 502, a device discovery procedure where the user device 120 discovers the wearable device 110 and, further, identifies the wearable device 110 as one that is transmitting the emergency information is carried out.

In an example in this regard, in case the second user 102 detects or suspects a medical emergency concerning the first user 101, the second user 102 may operate the user device 120 to initiate actions that enables transfer of the emergency information from the wearable device 110. According to an example, the user operation in this regard may involve activation of the emergency assistant gateway application in the user device 120, which application is arranged to respond to the activation by carrying out a device discovery procedure in order to discover a device that runs an emergency assistant data source application, e.g. in the wearable device 110. In this regard, the device discovery procedure may include, for example, the user device 120 scanning for beaconing messages from the wearable device 110 (and/or from any other wearable devices in vicinity). In case the wearable device 110 of the first user 101 is operational, it may be transmitting beaconing messages and the user device 120 may receive, via the first wireless link 150, one or more beaconing messages that carry the emergency information from the wearable device 110. The user device 120 may detect a message as a beaconing message that includes the emergency information on basis of the predefined emergency ID included in the received message or in a packet carrying the received message.

As a response to the beaconing message(s), the user device 120 may initiate a call to a party hosting the emergency service entity 130, as indicated in step 504 and further to establish the second wireless link 160 that connects the user device 120 to the emergency service entity 130. Once the second wireless link 160 is available, the user device 120 establishes a communication channel between itself and the emergency service entity 130, as indicated in step 506, and relays the emergency information received in the beaconing message to emergency service entity 130 using the established communication channel, as indicated in step 508. The user device 120 may further receive one or more further emergency messages from the wearable device 110 and relay the emergency information received in these messages to the emergency service entity 130 using the established communication channel therebetween, as indicated in step 510. Herein, the continued transfer of emergency information based on the further emergency messages may be carried out e.g. on basis of requests according to the second communication protocol outlined by the example described in the foregoing.

The initiation of the emergency call (step 504) may involve e.g. automatically calling to the emergency service number (such as 112 in Europe, 999 in the United Kingdom, or 911 in the United States). In a variation of this example, instead of automatically placing the call to a party hosting the emergency service entity 130, the emergency assistant gateway application may prompt the second user 102, via the user interface of the user device 120, to place the call to the party hosting the emergency service entity 130. In another variation of this example, the operation of block 220 (step 504) takes place before the step 502, thereby reversing the chain of events such that the second user 102 operates the user device 120 to place a call to the emergency services number (to a destination that also hosts the emergency service entity 130), whereas placing the call triggers the emergency assistant gateway application in the user device 120 to carry out the device discovery procedure by initiating the scanning for beaconing messages originating from the wearable device 110 via the first wireless link 150.

In an example, the wearable device 110 comprises a user operable key, button or activation means of another type that enables a user to activate the emergency assistant data source application therein to start transmitting the beaconing messages, possibly followed by the further emergency messages. An example of activation means of another type comprises a user interface (UI) element provided via a touchscreen or a touchpad, where the activation may be carried out by the user touching the UI element in a predefined manner (e.g. by touching the UI element for a time period that exceeds a predefined time threshold value and/or by touching the UI element using a force that exceeds a predefined threshold e.g. such that the user applies pressure that exceeds a predefined pressure threshold value). In another example, the emergency assistant data source application in the wearable device 110 may operate to detect a condition that indicates a potential medical emergency and/or to detect a condition that is likely to lead to a medical emergency of the first user 101 wearing the wearable device 110. As an example of the former, the sensor(s) 119 may comprise a heart rate sensor that is arranged to provide a respective time series of measurement values that are descriptive of the current heart rate of the first user 101. The emergency assistant data source application may monitor the heart rate on basis of these measurement values, and an observed heart rate that is below or above a respective predefined threshold or an observed change in heart rate that indicates abnormal heart operation may serve as an indication of a condition that indicates a potential medical emergency. As an example of the latter, the sensor(s) 119 may comprise an accelerometer that is arranged to provide a respective time series of measurement values that are descriptive of the measured acceleration, which is assumed to represent acceleration experienced by the first user 101. The emergency assistant data source function may monitor the acceleration on basis of these measurement values, and an observed acceleration or an observed change in acceleration exceeding a respective predefined threshold may serve as an indication of a condition that is likely to lead to a medical emergency. In response to detecting such a condition the emergency assistant data source application in the wearable device 110 initiates transmission of beaconing messages therefrom, which enables the user device 120 carrying out the device discovery procedure by scanning the beaconing messages to detect and receive the beaconing message(s) via the first wireless link 150.

In an example, the wearable device 110 is operated in a power-saving mode when the sensor(s) 119 do not suggest a condition that indicates a potential medical emergency and/or a condition that is likely to lead to a medical emergency of the first user 101 wearing the wearable device 110. Conversely, the wearable device 110 may be operated in an active mode (or the mode of operation may be changed from the power-saving mode to the active mode) in response to the sensor(s) 119 suggesting a condition that indicates a potential medical emergency and/or a condition that is likely to lead to a medical emergency of the first user 101 wearing the wearable device 110. In this regard, some parts to the wearable device, e.g. the communication apparatus 112, may be switched off in the power-saving mode but activated in the active mode of the wearable device 110. A switch or routing operation may be used to enable the active mode and the power-saving mode.

In a further embodiment, the processor 116 in the wearable device 110 may be arranged to control the antenna and the radio power of the communication portion 112. The processor can be coupled to the sensors 119 that provide the (respective) measurement values, which may be analyzed, e.g. by the processor 116, using one or more predefined analysis algorithms. One or more predefined analysis algorithm may be arranged select measurement values to be transmitted in the emergency information and/or time of transmitting the (selected) measurement values in the emergency information. Based on this analysis, one or more predefined thresholds may be applied to determine when to activate the operation of the communication portion 112 (or a radio or transceiver portion thereof) for transmission of the beaconing message. In an example, also the transmission frequency to be applied for transmitting the beaconing message may be determined on basis of the analysis.

In some examples of the embodiment, the emergency information may classified into one of predefined levels or classes, e.g. as one of "critical", "non-critical", "for information only", and an indication of the outcome of this classification may be included in the emergency data (e.g. in the beaconing message and/or in one or more further emergency messages). Consequently, the indicated classification may be applied in the user device 120 to selectively activate the emergency assistant gateway application, e.g. such that only emergency information indicates to represent one of one or more predefined levels/classes (e.g. "critical" or "non-critical") result in activation of the emergency assistant gateway application. In an example, the emergency information or its indicated level/class may trigger initiation of connection establishment between the wearable device 110 and the user device 120 to enable transfer of further emergency information. In another example, only one indication of emergency data can be determined in the wearable device 110 for transmission to the user device 120 to activate the emergency assistant gateway application therein and to initiate the call to the destination hosting the emergency service entity 130 (which initiation may take place either automatically or in response to a user action received via the user interface of the user device 120).

In an example, at least part of the emergency information transmitted from the wearable device 110 in the beaconing messages and/or in the further emergency messages is encrypted using any suitable encryption technique known in the art. As an example, the personal information, or at least the user identifier therein, may be included in the encrypted portion of the emergency information to keep from revealing the identity of the first user 101 to the second user 102 (i.e. the user of the user device 120) or to any third party who may be able to intercept the emergency information transferred from the user device 120 to the emergency service entity 130. The encryption may be carried out by using a predefined encryption key, whereas decryption by the emergency service entity 130 may be carried out using the same encryption key, while the user device 120 does not have knowledge of the encryption key. The encryption key may be created and/or shared between the wearable device 110 and the emergency service entity 130 upon pre-registering the user identifier of the first user 101 with the emergency service entity 130 (as described in the foregoing). Consequently, if the encryption is employed, the user device 120 has no access to the encrypted portion of the emergency information, and hence the encrypted portion of the emergency information is, at least conceptually, carried from the wearable device 110 to the emergency service entity 130 via a secure communication channel. Regardless, the user device 120, at least conceptually, serves as a gateway that connects the wearable device 110 to the emergency service entity 130 and hence relays the emergency information as received from the wearable device 110 to the emergency service entity 130. This 'gateway operation' in the user device 120 may be provided under control of the emergency assistant gateway application.

The user device 130 may further complement the emergency information received from the wearable 110 device in the beaconing message and/or in one or more further emergency messages by further information that may be useable in the emergency service entity in context of the emergency assistance service. As an example in this regard, the user device 110 may extract a device identifier assigned for the wearable device 110 from beaconing messages and/or further emergency messages received therefrom (or from packets or data structures of other type used to carry the respective message) and transmit the device identifier as part of the emergency information to the emergency service entity 130. If the device identifier has been pre-registered (e.g. by the user of the wearable device 110) with the emergency service entity 130, the device identifier may serve as an identification of the first user 101 wearing the wearable device 110. Due to this pre-registration procedure, the device identifier may be provided from the user device 120 to the emergency service entity 130 without encryption since the mapping between the identity of the first user 101 and the device identifier of the wearable device 110 is not available to any third party who may be able to intercept the emergency information transferred from the user device 120 to the emergency service entity 130.

The emergency information transferred from the wearable device 110 in the further emergency messages may depend on requests transmitted from the emergency service entity 130. As an example, the transfer of emergency information in the further emergency messages may include one-time transfer of the personal information, the static medical information and the medical history information, whereas the dynamically updated medical information may be transferred from the wearable device 110 continuously or periodically as long as the wearable device 110 is able to continue transmission of the further emergency messages and/or as long as the connection between the user device 120 and the emergency service entity 130 via the wireless link 160 is available.

The communication channel between the user device 120 and the emergency service entity 130 is independent of the voice channel that is initiated by the call from the user device 120 to the party hosting the emergency service entity 130 (e.g. the emergency call to the applicable emergency service number 112, 999 or 911). Hence, although typically initiated in parallel with the call, the transfer of emergency information via the communication channel may be carried independently of the presence of the voice channel, i.e. before activation of the voice channel, during presence of the voice channel and/or after closing the voice channel. Consequently, the emergency services center may be able to obtain first pieces of information concerning the first user 101 and his/her medical condition already before the emergency call while it may also be able to obtain continued updates of the medical condition of the first user 101 also after the emergency call has been completed.

The user device 120 may be arranged to display any unencrypted emergency information received from the wearable device 110 in the beaconing message and/or in the further emergency messages via a display of the user interface of the user device 120. This way, the user 102 may be able to directly see at least part of the emergency information and he/she may be able to further (verbally) provide at least some this information to the personnel at the destination hosting the emergency service entity 130 via the (emergency) call between the user device 120 and the emergency service entity 130. The beaconing message and/or in the further emergency messages may be chained or linked as a sequence of emergency messages that originate from the same wearable device 110 e.g. on basis of the user identifier and/or the device identifier.

In the example described in the foregoing, an implicit assumption is that the establishment of the first wireless link 150 in response to the device discovery carried out by the user device 120 takes place automatically in case a wearable device (such as the wearable device 110) that runs the emergency assistant data source application is discovered. In other examples, an explicit selection of the wearable device may be required as a condition for proceeding with establishment of the first wireless link 150 (and subsequent establishment of the secure communication channel between the discovered wearable device 110 and the emergency service entity 130). Herein, we refer such functionality as a selection mechanism. The selection mechanism may be provided in the wearable device 110 and/or in the user device 120. The selection mechanism may be a user controllable one or it may be at least partially automated one.

In an example, the selection mechanism may comprise selecting a wearable device that is closer than a predefined distance from the user device 120, whereas a wearable device that is further away from the user device 120 is left unselected (and hence no wireless link thereto is established). In this regard, the distance between a wearable device and the user device 120 may be estimated e.g. on basis of a received signal strength indicator (RSSI) computed on basis of one or more radio signals received in the user device 120 in the course of device discovery carried out in an attempt to detect the wearable device 110, e.g. such that a RSSI that exceeds a predefined threshold value is considered as an indication of a wearable device that is closer than the predefined distance.

In an example, two or more predefined threshold values may be used to enable classification of the distance between the wearable device 110 and the user device 120 into respective two or more proximity classes. This may involve for example, a first threshold value, a second threshold value and a third threshold value (listed in an increasing order of value), each associated with a respective proximity class. In particular, if the computed RSSI exceeds the first threshold value, the wearable device 110 is assigned to the first proximity class (e.g. "far"), if the computed RSSI exceeds the second threshold value, the wearable device 110 is assigned to the second proximity class (e.g. "near"), and if the computed RSSI exceeds the third threshold value, the wearable device 110 is assigned to the third proximity class (e.g. "immediate"). The user device 120 may transmit an indication of the assigned proximity class to the emergency service entity 130 (as a complement to the emergency information received from the wearable device 110) and/or display an indication of the assigned proximity class via a display of the user interface of the user device 120.

In another example, the selection mechanism may comprise a key, a button, a touch or an activation means of another type arranged in the wearable device 110, arranged to operate such that a user operating the activation means results in the wearable device 110 transmitting to the user device 120 a predefined activation signal or command that results in the user device 120 selecting the wearable device from which the activation signal/command originates. In a further example, the selection mechanism may comprise providing, via the user interface of the user device 120, an indication of a discovered wearable device and a selection means that enables the user to either select or ignore the discovered wearable device. The indication provided via the user interface of the user device 120 may include e.g. a device identifier and/or a user identifier associated with the discovered wearable device.

The selection mechanism may be particularly applicable in a scenario where there is, in addition to the wearable device 110, at least one further wearable device that runs a respective instance of the emergency assistant data source application within the operating range of the communication apparatus 122. A typical example of such a scenario is a case where the second user 102 is also wearing a wearable device (similar to the wearable device 110) of his/her own. In such a scenario, the selection mechanism may enable selection of the wearable device with which the first wireless link 150 is to be established from a plurality of (e.g. two or more) discovered wearable devices.

To cover such a scenario, the selection mechanism may further comprise selecting the wearable device that is closest to the user device 120. As an example in this regard, the distance between each discovered wearable device and the user device 120 may be estimated e.g. on basis of a respective received signal strength indicator (RSSI) computed on basis of one or more radio signals received in the user device 120 in the course of device discovery, and the selection may involve selecting the wearable device for which the highest RSSI has been computed (possibly further requiring that the RSSI also exceeds the predefined threshold value, as described in the foregoing). In another example, the selection mechanism may comprise providing, via the user interface of the user device 120, respective indications of two or more discovered wearable devices and a selection means that enables the user to select the desired one of the indicated wearable devices. As described above, an indication of a wearable device may include e.g. a device identifier and/or a user identifier associated with the respective discovered wearable device.

Figure 7:
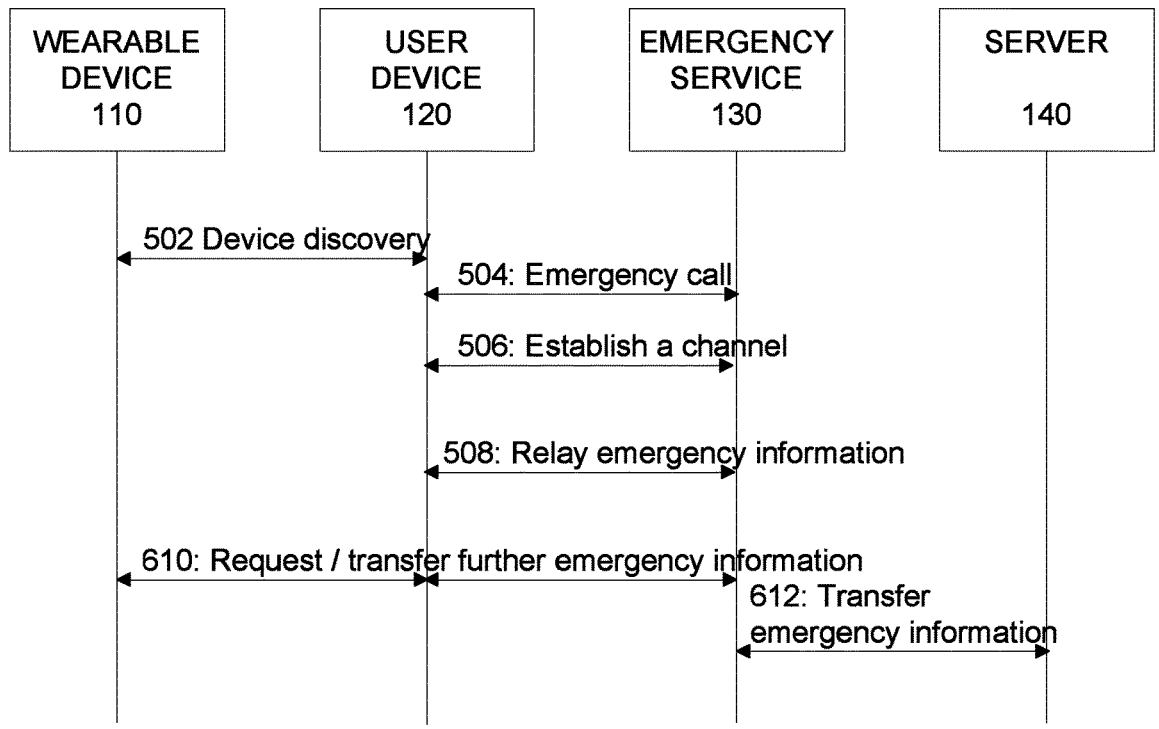
FIG. 7 illustrates a signal sequence diagram according to an example embodiment.

In a variation of the emergency assistance service described in the foregoing, at least part of the emergency information is accessible in the server device 140 and, hence, the emergency service entity 130 may obtain respective pieces of the emergency information from the server device 140 instead of the wearable device 110, whereas some pieces of the emergency information are transferred from the wearable device 110. The access to the emergency information in the server device 140 may be controlled by an emergency assistant server function or emergency assistant server application running in the server device 140. FIG. 7 depicts an example of establishing the secure communication channel and transfer of information between elements of the arrangement 100 in context of the emergency assistance service.

In the example of FIG. 7, the steps 502 to 508 may be carried in a similar manner as described in the foregoing in context of the example of FIG. 6, whereas the transfer of emergency information in steps 610 and 612 is different from that of the example of FIG. 6 (in step 510). In particular, only part of the emergency information is transferred to the emergency service entity 130 from the wearable device 110 while part of the emergency information is transferred from the server device 140. As an example in this regard, the emergency information transferred from the wearable device 110 to the emergency service entity 130 in step 610 may include a user identifier that uniquely identifies the first user 101 (as included in the personal information available in the wearable device 110) and possible also the dynamically updated medical information and/or the environmental information, whereas the static medical information, the medical history information and the remaining pieces of the personal information are available and may be transferred to the emergency service entity 130 from the server device 140 in step 612. In this regard, the user identifier received from the wearable device 110 (in step 610) enables the emergency service entity 130 to identify the static medical information, the medical history information and the remaining pieces of the personal information available in the server device 140 and request pieces of information considered relevant therefrom.

To facilitate the emergency service entity 130 accessing the selected pieces of emergency information in the server device 110, these pieces of emergency information may be transferred from the wearable device 110 to the server device 140 before the medical emergency for subsequent access by the emergency service entity 130. As an example in this regard, a user may operate an aspect of the emergency assistant data source application in the wearable device 110 to upload desired pieces of emergency information from the wearable device 110 to the server device 140. As another example, the wearable device 110 may be automatically, e.g. periodically, upload at least some pieces of emergency information to the server device 140. As a particular example, the automatic uploading may concern medical history information that may be continuously updated on basis of information obtained from respective ones of the sensor(s) 119.

The server device 140 is typically a remote server device that is arranged to provide the emergency assistant server application and that may be accessible by a number of emergency service entities 130. Although described herein, for editorial clarity of description, as function or application provided by a single server device entity, the emergency assistant server application may, alternatively, be jointly provided by a number of server devices that are arranged to provide a cloud service or a cloud server arrangement.

In the following, a number of non-limiting further examples concerning some aspects of the emergency assistance service are described, In one example, the communication apparatus 112 in the wearable device 110 and the communication apparatus 122 in the user device comprise respective BLE apparatuses. In such a case the wearable device 110 may be provided e.g. as a BLE tag, which is coupled to the one or more sensors 119. In such an arrangement, when the emergency assistant data source function in the wearable device 110 detects at least one of the sensors 119 to indicate a condition that meets a respective predefined threshold, the BLE apparatus is activated to start advertising an emergency condition using a predefined advertising message as the emergency message (also referred to as the beaconing message in the foregoing). The user device 120 runs the emergency assistant gateway application, which causes the user device 120 to scan other devices nearby and to detect the emergency message transmitted from the wearable device 110 if it is within an operating range of the BLE. The emergency message transmitted from the wearable device 110 includes the predefined emergency ID to identify the advertising message as the emergency message.

The emergency message so transmitted further includes, as the emergency information, one or more other items such as the sensor readings that triggered the emergency message, a predicted or a predefined reason for the advertised emergency, and an indication of a medical device (e.g. a defibrillator) that is likely needed to enable suitable medical assistance. In response to the emergency message, the user device 120, which runs the emergency assistant gateway application, may initiate the emergency call to the emergency service entity 130 and to forward or route the emergency information received in the emergency message to the emergency service entity 130. In one example, the user may activate a video camera or a (still) camera in the user device 120 by clicking camera icon provided in a user interface of the emergency assistant gateway application provided via the user interface of the user device 120 to capture a video stream or one or more images. Thus the emergency information received in the emergency service entity 130 may comprise data from the wearable device 110 together with real time image(s), real-time video stream and/or real time audio stream originating from the user device 120. In one embodiment when the user device 120 and the wearable device 110 are connected, the camera icon may, alternatively or additionally, serve as an actuator for activating capture of video stream or one or more images by using a video camera or a (still) camera in the wearable device 110. In such a scenario the emergency information that is received in the user device 120 from the wearable device 110 and that is relayed from the user device 120 to the emergency service entity 130 may further comprise the video stream and/or the one or more images originating from the wearable device 110. Medical personnel operating the emergency service entity 130 interprets the emergency information received from the user device 120 and information received from the user of the user device 120 in the emergency call and makes a decision concerning required actions.

In an example, if the wearable device 110 comprises a BLE apparatus as the communication apparatus 112, it may be arranged to operate as an iBeacon transmitter in response to detecting at least one of the sensors 119 to indicate a condition that meets the respective predefined threshold. This may be applicable, for example, in a scenario where the functionality described in the foregoing for the wearable device 110 is integrated to the user device 120 provided e.g. as a smartphone, as a smart watch, or as another mobile device typically carried with the second user 102. In another example, such a user device 120 having the functionality described in the foregoing for the wearable device 110 may be arranged to selectively use the BLE apparatus in one of the following ways: the user device 120 may use the BLE apparatus for operation as an iBeacon transmitter in response to detecting at least one of the sensors 119 to indicate a condition that meets the respective predefined threshold, or the user device 120 may use the BLE apparatus to scan for beaconing messages from (other) wearable devices 110. Thus the user device 120 may have two different ways to act as a scanning device or as a transmitting device In an example, the wearable device 110 comprises a BLE apparatus as the communication apparatus 112 that is configured to operate as an iBeacon device arranged to transmit advertising messages in a predefined format, which includes a predefined iBeacon prefix, followed by a variable Universally Unique Identifier (UUID), a major part and a minor part. In this regard, the BLE apparatus may continuously transmit the advertising messages including the UUID assigned for emergency services to distinguish it from iBeacon transmitters serving some other purpose.

Herein, the UUID may serve as the emergency ID described in the foregoing. The major may be applied to carry respective indications of general medical status of the user of the wearable device 110 and possible actions to be taken in case of emergency (e.g. an indication of diabetes and an indication of an appropriate dose of insulin to be applied as the cure) and the minor may be applied to carry further details concerning user (e.g. further medical history information) and/or other information that species characteristic(s) of the BLE apparatus as iBeacon transmitter. Other parts of the advertising message may be applied to carry further emergency information, e.g. most recently obtained readings from the sensors 119. In an example, the wearable device 110 may function as a slave of a BLE communication link while the user device 120 may function as a master of the BLE communication link, where the user device 120 as the master device transmits one or more device discovery requests (e.g. one or more scan requests) and the wearable device 110 as the slave device responds to one or more device discovery request by transmitting profile information, e.g. the emergency information.

In an example, a connection between the user device 120 and the wearable device 110 may be established via the first wireless link 150, and the user device 120 may use the established connection to activate an actuator, such as a loudspeaker, in the wearable device 110 to play a predefined sound to facilitate the second user 102 to locating the wearable device 110.

In an example of the embodiment, when the user device 120 and the wearable device 110 are owned by the same person or they are owned by the family members or friends or other trusted persons, the user device 120 and the wearable device 110 may be paired and therefore (automatically) connected when within an operating range from each other. In such situations when the emergency in wearable device 110 is recognized, reception of a beaconing message from the wearable device 110 will cause the user device 120 make a call to the destination hosting the emergency service entity 130 in automated manner. Thus, some aspects of the procedures for transmitting the beaconing message from the wearable device 110 to the user device 120 and/or for initiating the call to the destination hosting the emergency service entity 130 may be dependent on the relationship between the wearable device 110 and the user device 120 in terms of their ownership.

In one example, the emergency assistant data source function/application in the wearable device 110 operates to transmit as one piece of the emergency information a uniform resource locator (URL) for the user device 120 to relay to the emergency service entity 130. The URL can be accessed by the emergency assistant data source function/application. In the regard, the emergency service entity 130 may have been provided with required access rights to the URL (in case such authorization is required) as part of the pre-registration the first user 101 may have carried out with the emergency service entity 130. In the URL, further emergency information and/or other data associated with the first user 101 may be made available for the emergency service entity 130 to download.

Figure 8:
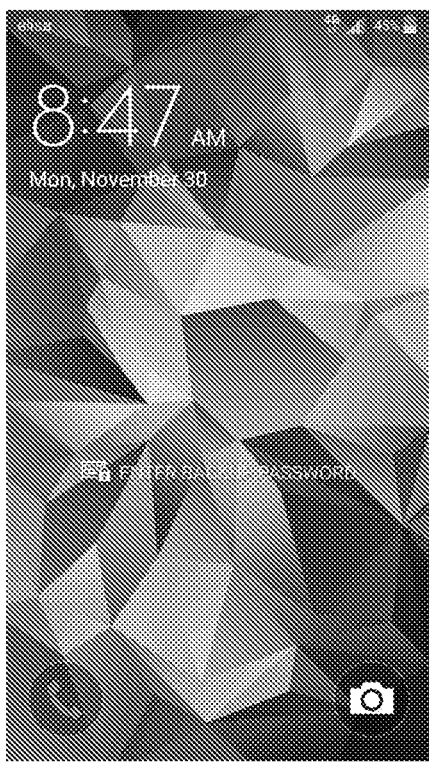
FIG. 8 illustrates an example of an aspect of user interface according to an example embodiment.
Figure 8:
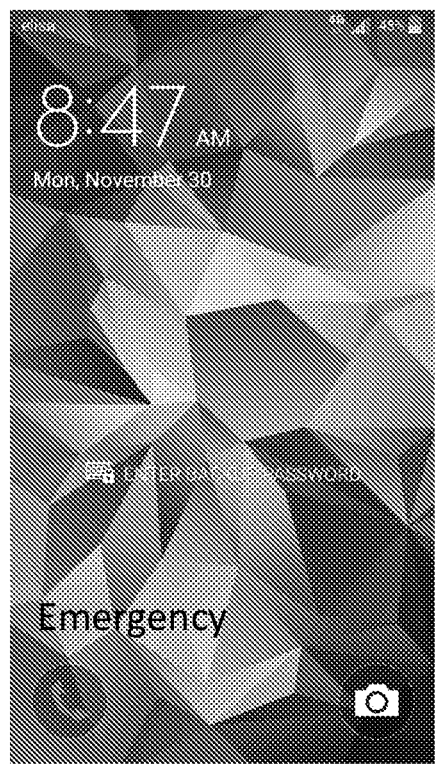

In the following, some examples of an embodiment concerning user interface aspects related to the emergency assistant gateway function or application in the user device 120 and/or use thereof are described. In this regard, illustration A of FIG. 8 depicts a known way to provide so-called lock screen of a mobile device such as a smartphone, while illustration B of FIG. 8 depicts a similar lock screen augmented with a user interface element that enables the user of the user device 120 to activate the emergency assistant gateway application. In one example, a visual identifier of a medical emergency may be provided in the screen in response to receiving a beaconing message from the wearable device 110. In the example illustrated in FIG. 8, the medical emergency of the first user 101 wearing the wearable device 110 is indicated by the text "Emergency" appearing in the lock screen. Instead of using the text "Emergency", e.g. a textual description that characterizes the cause of the medical emergency and/or a non-textual visual indication (e.g. an image) may be applied as an indication of the medical emergency. Consequently, the user of the user device 120 may initiate the call to the destination hosting the emergency service entity 130 (e.g. an emergency call) and to initiate transfer of the emergency data to the emergency service entity 130 by a sliding a finger on the screen from the handset icon to the visual indication of the medical emergency. Further visual cues such as blinking of the visual emergency indication, audible cues such as playing back a predefined alarm sound, or tactile cues such as a vibration alert may applied instead or in addition to showing the visual emergency indicator in the screen of the user device 120. The call to the destination hosting the emergency service entity 130 and relaying of the emergency information received from the wearable device 110 (in the beaconing message and possibly in one or more further emergency messages) to the emergency service entity 130 may be provided without exiting the lock screen. Moreover, e.g. a camera application in the user device 120 may be made accessible via the lock screen in response to receiving the beaconing message from the wearable device 110.

Figure 9:
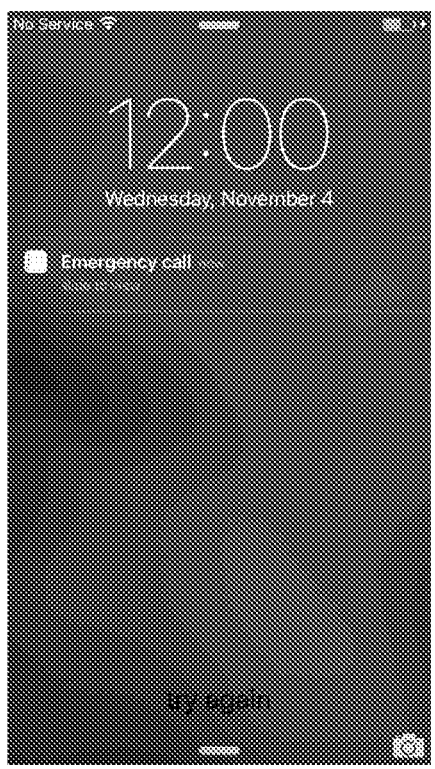
FIG. 9 illustrates an example of another aspect of user interface according to an example embodiment.
Figure 9:
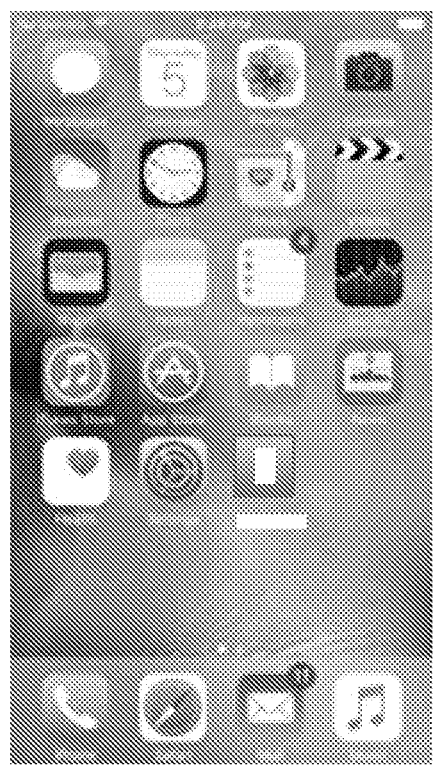

FIG. 9 provides a further example of the embodiment concerning usage of the emergency assistant gateway function or application in the user device 120 provided as a mobile phone or a smartphone. In particular, illustration A in FIG. 9 depicts another example of the lock screen, where an indication of an emergency is shown, e.g. in response to having received a beaconing message from the wearable device 110. Illustration B of FIG. 9 depicts a menu after exiting the lock screen e.g. by touching, tapping or sliding a finger on the screen at or close to the indication of the emergency displayed in the screen. The menu shows an icon that represents the emergency assistant gateway application in the user device 120, which in this example is shown as icon titled "Emergency" and depicting a capital E. In case a beaconing message indicating a medical emergency has been received from the wearable device 110, the icon that represents the emergency assistant gateway application may be shown in a color that is different from that applied in case no emergency has been detected and/or the icon may be blinking to facilitate attracting attention of the user of the user device 120.

Figure 10:
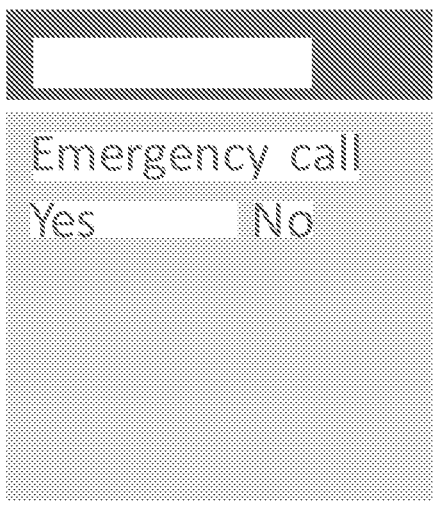
FIG. 10 illustrates an example of a further aspect of user interface according to an example embodiment.
Figure 10:
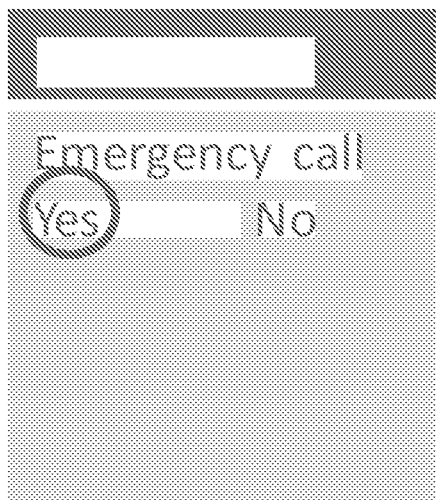
Figure 10:
Figure 10:

In response to the user activating the emergency assistant gateway application, e.g. by touching or tapping the screen at or close to the respective icon in the menu displayed on the screen, the operation proceeds to selective initiation of the emergency call (to the destination that hosts the emergency service entity 130), e.g. in accordance with illustration A of FIG. 10, where the user is provided with an option to initiate the emergency call or refrain from initiating the emergency call (again, e.g. by touching or tapping on the screen at or close to the respective indication in the screen). In case the user makes a selection to proceed with the emergency call, the procedure continues as indicated in illustrations B to D of FIG. 10: illustration B indicates the user of the user device 120 having selected to proceed with the emergency call, illustration C indicates that the emergency call has been initiated, and illustration D indicates that the emergency call has been answered at the destination that hosts the emergency service entity 130 and transmission of the emergency information thereto has been initiated and/or is currently being carried out.

Figure 11:
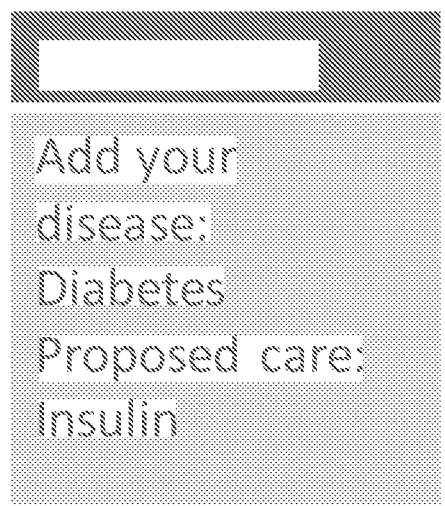
FIG. 11 illustrates an example of a further aspect of user interface according to an example embodiment.

FIG. 11 provides a further example of the embodiment, concerning usage of the emergency assistant data source function or application for configuration of the medical history data associated with the first user 101 of the wearable device 110. The data entry may be provided e.g. via the user device 120 using an aspect of the emergency assistant gateway application therein. In this regard, the aspect of the emergency assistant gateway function may provide the user with an option to enter an indication of the general medical status of the first user 101 and the respective actions to be taken in case of an emergency. The user may insert these pieces of information e.g. by tapping or touching the screen at or close to the respective indication displayed on the screen ("Add your disease", "Proposed care"), after which he/she will be given a possibility to type (or otherwise enter) the respective piece of information to be transmitted to the wearable device 110 and stored therein for subsequent use in the emergency information.

In the foregoing, references to the call to a destination hosting the emergency service entity 130 (e.g. an emergency all) refer to a voice call over a voice channel between the user device 120 and the destination (e.g. an emergency service center, a hospital, an emergency vehicle, etc.). However, there may be situations where a user of the user device 120, e.g. the second user 102, cannot speak. As non-limiting examples, such a situation may arise e.g. in a scenario where the user 102 of the user device 120 is also wearing the wearable device 110 or in a scenario where the functions of the wearable device 110 are at least in part integrated to the user device 120, and the medical emergency pertaining to the second user 102 makes it difficult or impossible for him/her to speak while the user device 120 is arranged to place the call to the destination hosting the emergency service entity 130 automatically in response to receiving the beaconing message. In this regard, the wearable device 110 may detect, e.g. based on measurement values from one or more sensors 119, a condition where the user is not likely able to speak and transmit a predefined signaling tone via the voice channel to the destination hosting the emergency service entity 130. An example of detecting such a condition using the measurement values from the sensor 119 involves receiving measurement values from an accelerometer arranged in the wearable device 110 and detecting the received measurement values to indicate no movement or only small movement of the user (which detection may comprise a measurement values from the accelerometer indicating movement that is less than a predefined threshold over a predefined time period). The predefined signaling tone may be provided e.g. as a predefined sequence of dual-tone multi-frequency (DTMF) signals (e.g. as a sequence that corresponds to dialing a sequence "55" using a keypad of a phone). The signaling tone may be transmitted from the user device 120 after a predefined time delay from initiation of the voice call and/or repeated a predefined number of times at predefined time intervals.

Referring back to components of the wearable device 110, the user device 120 and the emergency service entity 130, the processor 116, 126, 136 is configured to read from and write to the respective memory 115, 125, 135. Although each of the processors 116, 126, 136 is depicted as a respective single component, any of the processors 116, 126, 136 may be implemented as respective one or more separate processing components. Similarly, although each of the memories 115, 125, 135 is depicted as a respective single component, any of the memories 115, 125, 135 may be implemented as respective one or more separate components, some or all of which may be integrated/removable and/or may provide permanent/semi-permanent/dynamic/cached storage.

The memory 115, 125, 135 may store the respective computer program comprising computer-executable instructions that control the operation of the respective device 110, 120, 130 when loaded into the respective processor 116, 126, 136. As an example, the computer program may include one or more sequences of one or more instructions. Using components of the user device 120 as an example, the computer program may be provided as part of the computer program code 127. The processor 126 is able to load and execute the computer program by reading the one or more sequences of one or more instructions included therein from the memory 125. The one or more sequences of one or more instructions may be configured to, when executed by the processor 126, cause the user device 120 to carry out operations, procedures and/or functions described in the foregoing in context of the emergency assistance service. Hence, the user device 120 may comprise at least one processor 126 and at least one memory 125 including the computer program code 127 for one or more programs, the at least one memory 125 and the computer program code 127 configured to, with the at least one processor 126, cause the user device 120 to perform operations, procedures and/or functions described in the foregoing in context of the emergency assistance service. Similar considerations are equally valid for corresponding components 11x of the wearable device 110 and for corresponding components 13x of the emergency service entity 130.

The computer programs stored in any of the memories 115, 125, 135 may be provided e.g. as a respective computer program product comprising at least one computer-readable non-transitory medium having the respective computer program code 117, 127, 137 stored thereon, the computer program code, when executed by the respective device 110, 120, 130, causes the device at least to perform operations, procedures and/or functions described in the foregoing in context of the respective device 110, 120, 130 in description of operation of the emergency assistance service. The computer-readable non-transitory medium may comprise a memory device or a record medium such as a CD-ROM, a DVD, a Blu-ray disc or another article of manufacture that tangibly embodies the computer program. As another example, the computer program may be provided as a signal configured to reliably transfer the computer program.

Reference(s) to a processor should not be understood to encompass only programmable processors, but also dedicated circuits such as field-programmable gate arrays (FPGA), application specific circuits (ASIC), signal processors, etc.

Features described in the preceding description may be used in combinations other than the combinations explicitly described. Although functions have been described with reference to certain features, those functions may be performable by other features whether described or not. Although features have been described with reference to certain embodiments, those features may also be present in other embodiments whether described or not.

The invention claimed is:

1. A method comprising:
    receiving, at a user device, a beaconing message from a wearable device, the beaconing message received over a first wireless link, the beaconing message comprising emergency information associated with a user wearing the wearable device, and the beaconing message being generated in response to the wearable device detecting an emergency based at least on one or more measurements of a vital sign of the user wearing the wearable device;
    in response to the beaconing message, initiating, at the user device, an emergency call to an emergency service entity; and
    relaying, by the user device, the emergency information received in the beaconing message from the wearable device to the emergency service entity, the emergency information relayed to the emergency service entity via a second wireless link, the emergency information comprising a device identifier of the wearable device, wherein the device identifier mapped to an identity of the user based on registration of the device identifier with the emergency service entity, and the device identifier being relayed to the emergency service entity to at least enable the emergency service entity to identify, based at least on a mapping between the device identifier and the identity of the user, the user associated with the wearable device,
    wherein the user device display unencrypted emergency information received from wearable device.

2. A method according to claim 1, further comprising:
    responding to a request received via a user interface of the user device by at least initiating, at the user device, a scan for the beaconing message comprising the emergency information.

3. A method according to claim 1, wherein the wearable device includes and/or is coupled with one or more sensors configured to generate the one or more measurements of the vital sign of the user wearing the wearable device, and wherein the wearable device detects the emergency by at least analyzing the one or more measurements of the vital sign.

4. An apparatus comprising a first communication apparatus for wireless communication via a first wireless link and a second communication apparatus for wireless communication via a second wireless link, the apparatus configured to at least:
    receive, from a wearable device, a beaconing message, the beaconing message received over the first wireless link, the beaconing message comprising emergency information associated with a user wearing the wearable device, and the beaconing message being generated in response to the wearable device detecting an emergency based at least on one or more measurements of a vital sign of the user wearing the wearable device;
    in response to the beaconing message, initiate an emergency call to an emergency service entity; and
    relay, from the wearable device to the emergency service entity, the emergency information received in the beaconing message, the emergency information relayed to the emergency service entity via the second wireless link, the emergency information comprising a device identifier of the wearable device, wherein the device identifier mapped to an identity of the user based on registration of the device identifier with the emergency service entity, and the device identifier being relayed to the emergency service entity to at least enable the emergency service entity to identify, based at least on a mapping between the device identifier and the identity of the user, the user associated with the wearable device,
    wherein the user device display unencrypted emergency information received from wearable device.

5. An apparatus according to claim 4, wherein the apparatus is further configured to at least:
    respond to a request received via a user interface of the apparatus by at least initiating a scan for the beaconing message comprising the emergency information.

6. An apparatus according to claim 4, wherein the apparatus is further configured to at least:
    activate an emergency service application to trigger the initiation of the emergency call and the relay of the emergency information to the emergency service entity.

7. An apparatus according to claim 4, wherein the beaconing message includes a predefined emergency indication to identify the beaconing message as an emergency message that includes the emergency information.

8. An apparatus according to claim 4, wherein at least part of the emergency information received from the wearable device is encrypted.

9. An apparatus according to claim 4, wherein the relay of the emergency information comprises:
    establishing the second wireless link between the apparatus and a network that connects the apparatus to the emergency service entity; and establishing, between the apparatus and the emergency service entity, a connection for transferring the emergency information, the connection established via the second wireless link.

10. An apparatus according to claim 4, wherein the initiation of the emergency call comprises:
prompting, via a user interface of the apparatus, a user of the apparatus to initiate the emergency call;
initiating the emergency call in response to an user input received via the user interface.

11. An apparatus according to claim 4, wherein the emergency call is initiated automatically in response to the beaconing message.

12. An apparatus according to claim 4, further comprising:
selecting, in response to receiving a plurality of beaconing message from a plurality of wearable devices, one of the plurality of wearable devices, the one of the plurality wearable devices being selected based at least on the one of the plurality of wearable devices being closer than a predefined distance from the apparatus, the one of the plurality of wearable devices being closest to the apparatus, or having received a predefined activation signal from the one of the plurality of wearable devices.

13. An apparatus according to claim 4, further comprising:
selecting, in response to receiving a plurality of beaconing messages from a plurality of wearable devices, one of the plurality of wearable devices, the one of the plurality of wearable devices being selected by at least providing, via a user interface of the apparatus, an indication of the plurality of wearable devices discovered by performing a device discovery procedure, and receiving, via the user interface, a user selection of the one of the plurality of wearable devices.

14. An apparatus according to claim 4, wherein the emergency information further comprises at least one of a personal information associated with the user wearing the wearable device and an environmental information descriptive of one or more environmental characteristics in a vicinity of the wearable device.

15. An apparatus according claim 4, wherein the emergency information further includes medical information, and wherein the medical information includes the one or more measurements of the vital sign of the user and/or a medical history of the user.

16. An apparatus according to claim 4, wherein the apparatus is further configured to at least:
receive, from the wearable device, another message comprising additional emergency information, the other message received over the first wireless link; and
relay, to the emergency service entity, the additional emergency information via the second wireless link.

17. An apparatus according to claim 4, wherein the apparatus is further configured to at least:

display, based at least on the beaconing message, an indication of the emergency in an user interface of the apparatus; and
receive, via the user interface, a user input for initiating the emergency call in response to the indication of the emergency displayed in the user interface.

18. An apparatus according to claim 4, wherein the apparatus is further configured to at least:
capture a video stream and/or one or more images; and
transmit, to the emergency service entity, the video stream and/or the one or more images together with the emergency information.

19. An apparatus according to claim 4, wherein the apparatus further comprises at least one processor and a memory storing instructions that, when executed by the at least one processor, cause the apparatus to at least perform:
the receiving of the beaconing message;
the initiating of the call to the emergency service entity; and
the relaying of the emergency information.

20. A computer program product comprising a non-transitory computer readable medium storing instructions, which when executed by at least one data processor, result in operations comprising:
receiving, at a user device, a beaconing message from a wearable device, the beaconing message received over a first wireless link, the beaconing message comprising emergency information associated with a user wearing the wearable device, and the beaconing message being generated in response to the wearable device detecting an emergency based at least on one or more measurements of a vital sign of the user wearing the wearable device;
in response to the beaconing message, initiating, at the user device, an emergency call to an emergency service entity; and
relaying, by the user device, the emergency information received in the beaconing message from the wearable device to the emergency service entity, the emergency information relayed to the emergency service entity via a second wireless link, the emergency information comprising a device identifier of the wearable device, wherein the device identifier mapped to an identity of the user based on registration of the device identifier with the emergency service entity, and the device identifier being relayed to the emergency service entity to at least enable the emergency service entity
to identify, based at least on a mapping between the device identifier and the identity of the user, the user associated with the wearable device,
wherein the user device display unencrypted emergency information received from wearable device.

* * * * *